United States Patent
Jew et al.

(10) Patent No.: US 6,169,112 B1
(45) Date of Patent: Jan. 2, 2001

(54) MEDICINES FOR TREATING DEMENTIA OR COGNITIVE DISORDER, WHICH COMPRISES ASIATIC ACID DERIVATIVES

(75) Inventors: Sang Sup Jew; Hyeung Geun Park; Hee Doo Kim, all of Seoul; Young Hoon Jung, Kyunggi-do; Young Choong Kim; So Ra Kim, both of Seoul; Sung Ki Seo, Pusan; Tae Gyu Nam, Chungchongbuk-do; Ducky Han, Seoul; Chi Hyoung Yoo, Pusan; Doo Yeon Lim, Seoul; Jeong Hoon Kim, Seoul; Hee Man Kim, Seoul; Jae Ho Park, Seoul; Pil Jong Shim, Seoul; Ju Eun Jung, Seoul; Hee Young Beom, Seoul, all of (KR)

(73) Assignee: Dong Kook Pharmaceutical Co., Ltd. (KR)

( * ) Notice: Under 35 U.S.C. 154(b), the term of this patent shall be extended for 0 days.

(21) Appl. No.: 09/308,876

(22) PCT Filed: Nov. 27, 1997

(86) PCT No.: PCT/KR97/00238

§ 371 Date: May 25, 1999

§ 102(e) Date: May 25, 1999

(87) PCT Pub. No.: WO98/23278

PCT Pub. Date: Jun. 4, 1998

(30) Foreign Application Priority Data

Nov. 27, 1996 (KR) .................................. 96-58173

(51) Int. Cl.[7] .................................................. A01N 37/00
(52) U.S. Cl. .................................................. 514/557
(58) Field of Search .............................. 514/557

(56) References Cited

U.S. PATENT DOCUMENTS 5,834,437 * 11/1998 Jew et al. ............................... 514/25

FOREIGN PATENT DOCUMENTS

WO 96/17819 * 6/1996 (WO).

* cited by examiner

Primary Examiner—Barbara Badio
(74) Attorney, Agent, or Firm—Heslin & Rothenberg, P.C.

(57) ABSTRACT

Disclosed is the use of 2-oxoasiatic acid in the treatment of dementia or cognitive disorders.

1 Claim, No Drawings

MEDICINES FOR TREATING DEMENTIA OR COGNITIVE DISORDER, WHICH COMPRISES ASIATIC ACID DERIVATIVES

PRIOR FOREIGN APPLICATIONS

This application is a 35 USC §371 filing of PCT/KR97/00238, filed Nov. 27, 1997 and claims priority from KR patent application number 1996/58173, filed Nov. 27, 1996.

TECHNICAL FIELD

The present invention relates to novel medical use of asiatic acid derivatives and pharmaceutical compositions containing the same. More specifically, the present invention relates to a use of asiatic acid derivatives represented by general formula 1:

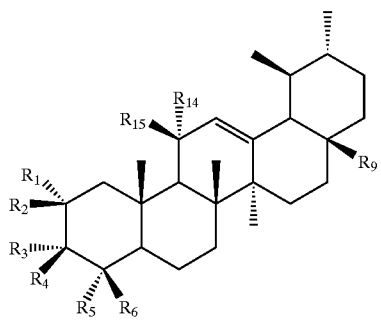

1 wherein, $R_1$ represents hydrogen, hydroxy group which may be protected by acetyl or benzyl group, methyl, ethyl, methoxy, ethoxy, vinyl, ethinyl, cyano, azide, ethoxymethyloxy, octyloxymethyloxy, methanesulfonyloxy, phenylthio group or (methylthio)thiocarbonyloxy group; $R_2$ represents hydrogen or hydroxy group which may be protected by acetyl or benzoyl group, methoxy or ethoxy group; $R_1$ and $R_2$ may form an oxo group; $R_3$ represents hydrogen, hydroxy group which may be protected by acetyl or benzoyl group, vinyl, methyl or ethyl group; $R_4$ represents hydrogen, methyl, ethyl, vinyl, or hydroxy group which may be protected by acetyl or benzoyl group; $R_2$ and $R_4$ may form an epoxy group; $R_3$ and $R_4$ may form an oxo group; $R_5$ represents methyl, hydroxymethyl group of which hydroxy group may be protected by acetyl or benzoyl group, tert-butyldimethylsilyloxymethyl group, carboxylic group, carboxylic ester moiety, carboxylic amide moiety or aldehyde group; $R_4$ and $R_5$ may form —$OCR_6R_7OCH_2$— [wherein, $R_6$ is hydrogen, a lower alkyl group having 1 to 4 carbon atoms, or phenyl group, $R_7$ represents hydrogen, a lower alkyl group having 1 to 4 carbon atoms or phenyl group, and $R_6$ and $R_7$ may form —$(CH_2)_5$—]; $R_8$ represents hydrogen or methyl group; $R_9$ represents —$CH_2COOR$ or —$COOR$ [wherein, R represents hydrogen, a lower alkyl group having 1 to 4 carbon atoms, 2-tetrahydropyranyl, $CH(OR_{11})R_{10}$, $CH(OR_{13})CH_2R_{12}$ (wherein, $R_{10}$ represents hydrogen, methyl or ethyl group, $R_{11}$ represents a lower alkyl group having 1 to 4 carbon atoms, octyl, benzyl, methoxymethyl or methoxyethyl group, $R_{12}$ represents hydrogen, methyl or ethyl group, $R_{13}$ represents methyl or ethyl group, or $R_{12}$ and $R_{13}$ may form —$CH_2CH_2CH_2$—), or glucosyl or rhamnosyl group], hydroxymethyl of which hydroxy group may be protected by acetyl or benzoyl group, methanesulfonyloxymethyl or cyanomethyl group; $R_{14}$ and $R_{15}$ independently represent hydrogen, or both form oxo group together

[provided that when $R_1$ is hydroxy, $R_2$ is hydrogen, $R_3$ is hydrogen, $R_4$ is hydroxy, $R_5$ is hydroxymethyl and $R_8$ is methyl, R does not represent hydrogen nor methyl, and $R_{10}$ does not represent hydrogen; and provided that when $R_1$ is hydroxy, $R_2$ is hydrogen, $R_3$ or $R_4$ may form, with $R_5$, —$OC(R_6)(R_7)OCH_2$—, and $R_6$ is methyl, R does not represent methyl group;

and pharmaceutically acceptable salts and esters thereof, for treating dementia or cognitive disorder.

BACKGROUND ART

Asiatic acid, madecassic acid and asiaticoside, trisaccharide of asiatic acid, which are compounds extracted from *Centella asiatica*, isolated firstly by Bontems in 1941 [J. E. Bontems, *Bull. Sci. Pharmacol.*, 49, 186–91(1941)] and their srtuctures were defined by Polonsky [J. Polonsky, *Compt. Rend.*, 232, 1878–80(1951); J. Polonsky, *Bull. Soc. Chim.*, 173–80(1953)].

The extracts including asiatic acid and asiaticoside from *Centella asiatica* have been used for tratment of hurted skin or chronic ulcer since old times, and also for treatment deformation of skin due to tuberculosis or leprosy [P. Boiteau, A. Buzas, E. Lederer and J. Polonsky, *Bull. Soc. Chim.*, 31, 46–51(1949)].

Recently, they have been reported to have some effect on dementia and cognitive disorder by Hoechst (EP 0383 171 A2). However, as can be seen from the experimental results described in the literature above, the remedial effect for treating dementia is so weak that the research for medicines to treat dementia with much stronger effect is still requested.

DISCLOSURE OF THE INVENTION

The present inventors have already synthesized various asiatic acid derivatives represented by chemical formula 1 as above and filed with the Korea Industrial Property Office as a patent application (Korean Patent Application No. 95-46131 and 96-58175), and also performed intensive studies on the asiatic acid derivatives, and found the fact that the derivatives of formula 1 are useful for treating dementia and cognitive disorder, to complete the invention.

The object of the present invention is to provide medicines for treating dementia or cognitive disorder, which contains asiatic acid derivatives of general formula 1 as an active component:

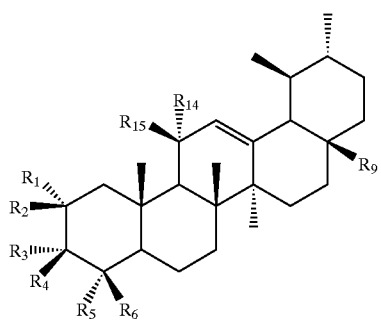

1 wherein, $R_1$ represents hydrogen, hydroxy group which may be protected by acetyl or benzyl group, methyl, ethyl, methoxy, ethoxy, vinyl, ethinyl, cyano, azide, ethoxymethyloxy, octyloxymethyloxy, methanesulfonyloxy, phenylthio group or (methylthio)thiocarbonyloxy group; $R_2$ represents hydrogen or hydroxy group which may be protected by acetyl or benzoyl group, methoxy or ethoxy group; $R_1$ and $R_2$ may form an oxo group; $R_3$ represents hydrogen, hydroxy group which may be protected by acetyl or benzoyl group, vinyl, methyl or ethyl group; $R_4$ represents hydrogen, methyl, ethyl, vinyl, or hydroxy group which may be protected by acetyl or benzoyl group; $R_2$ and $R_4$ may form an epoxy group; $R_3$ and $R_4$ may form an oxo group; $R_5$ represents methyl, hydroxymethyl group of which hydroxy group may be protected by acetyl or benzoyl group; tert-butyldimethylsilyloxymethyl group, carboxylic group, carboxylic ester moiety, carboxylic amide moiety or aldehyde group; $R_4$ and $R_5$ may form —$OCR_6R_7OCH_2$— [wherein, $R_6$ is hydrogen, a lower alkyl group having 1 to 4 carbon atoms, or phenyl group, $R_7$ represents hydrogen, a lower alkyl group having 1 to 4 carbon atoms or phenyl group, and $R_6$ and $R_7$ may form —$(CH_2)_5$—]; $R_8$ represents hydrogen or methyl group; $R_9$ represents —$CH_2COOR$ or —$COOR$ [wherein, R represents hydrogen, a lower alkyl group having 1 to 4 carbon atoms, 2-tetrahydropiranyl, $CH(OR_{11})R_{10}$, $CH(OR_{13})CH_2R_{12}$ (wherein, $R_{10}$ represents hydrogen, methyl or ethyl group, $R_{11}$ represents a lower alkyl group having 1 to 4 carbon atoms, octyl, benzyl, methoxymethyl or methoxyethyl group, $R_{12}$ represents hydrogen, methyl or ethyl group, $R_{13}$ represents methyl or ethyl group, or $R_{12}$ and $R_{13}$ may form —$CH_2CH_2C_2$—), or glucosyl or rhamnosyl group of which hydroxy group may be protected by acetyl or benzoyl group], hydroxymethyl of which hydroxy group may be protected by acetyl or benzoyl group, methanesulfonyloxymethyl or cyanomethyl group; $R_{14}$ and $R_{15}$ independently represent hydrogen, or both form oxo group [provided that $R_1$ is hydroxy, $R_2$ is hydrogen, $R_3$ is hydrogen, $R_4$ is hydroxy, $R_5$ is hydroxymethyl and $R_8$ is methyl, R does not represent hydrogen nor methyl, $R_{10}$ does not represent hydrogen; and provided that $R_1$ is hydroxy, $R_2$ is hydrogen, $R_3$ or $R_4$ forms, with $R_5$, —$OC(R_6)(R_7)$ $OCH_2$—, and $R_6$ is methyl, R does not represent methyl group; and pharmaceutically acceptable salts and esters thereof; for treating dementia or cognitive disorder.

In other words, the present invention relates to a use of asiatic acid derivatives represented by formula 1, and pharmaceutically acceptable salts and esters thereof, for treating dementia or cognitive disorder.

The treatment according to the invention includes rapid alleviation of symptoms or preventive measures.

The general preparation of compound of general formula 1 according to the present invention is presented by Korean patent application No. 95-46131, but in case that the definiton of general formula among compounds is general formula 2 below, it is is desirable to prepare by Method 1~8.

2

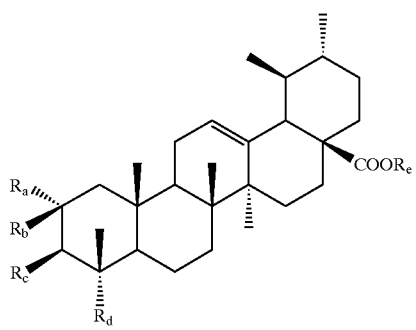

wherein, $R_a$ represents hydrogen, hydroxy group which may be protected by acetyl or benzyl group, methanesulfonyloxy, (methylthio) thiocarbonyloxy, halogen, ethoxymethyloxy or octyloxymethyloxy group; $R_b$ represents hydrogen or hydroxy group; $R_a$ and $R_b$ may form an oxo group; $R_c$ represents hydrogen or hydroxy group which may be protected by acetyl or benzoyl group; $R_b$ and $R_c$ may form an epoxy group; $R_d$ represents hydroxymethyl group which may be protected by acetyl or benzoyl group; $R_c$ and $R_d$ may form —$OC(R_f)(R_g)OCH_2$— [wherein, $R_f$ is hydrogen, a lower alkyl group having 1 to 4 carbon atoms, or phenyl group, $R_g$ represents hydrogen, a lower alkyl group having 1 to 4 carbon atoms or phenyl group, and $R_f$ and $R_g$ may form —$(CH_2)_5$—]; $R_e$ represents hydrogen, a lower alkyl group having 1 to 4 carbon atoms, an alkoxymethyl group having 1 to 4 carbon atoms, octyloxymethyl, methoxyethoxymethyl, benzyloxymethyl or 2-tetrahydropyranyl group.

The preparation of asatic acid derivative of chemical formula 2 above accordig to the present invention is presented below.

Method 1

Titrated extracts of *Centella asiatica* (TECA) is hydrolyzed to obtain a mixture of asiatic acid and madecassic acid, and the mixture is reacted with 2,2-dimethoxypropane in the presence of acid catalyst. The reaction product is purified by column chromatography to isolate 3,23-O-isopropylidene asiatic acid (3) in which 3,23-dihydroxy group is protected. The obtained product is treated with diazomethane to synthesize methyl 3,23-O-isopropylidene asiatate (4). [See Scheme 1.]

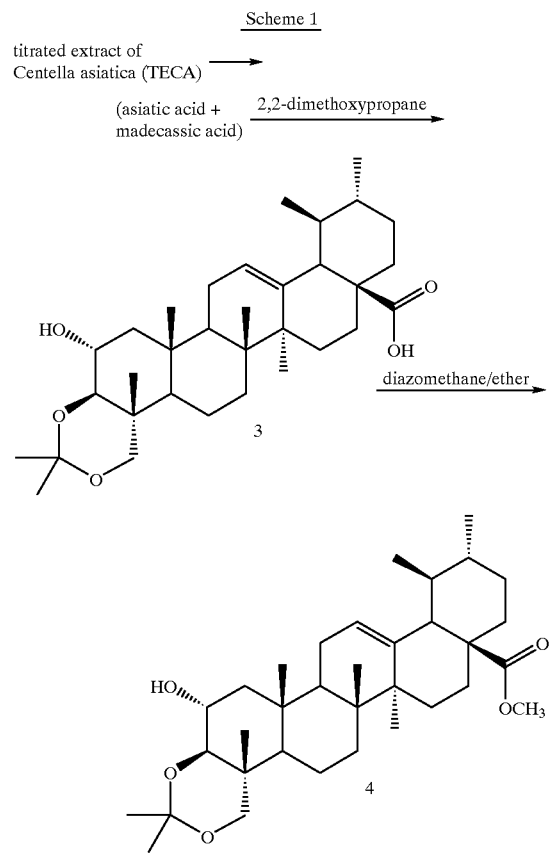

Method 2

Two hydroxy groups at 3- and 23-position of asiatic acid are protected with various ketone or aldehyde group to synthesize compounds represented by general formula (5).

[Provided that $R_f$=H and $R_g$=H, the compound is synthesized by the use of dimethyl sulfoxide and trimethylsilyl chloride.] The compound of general formula (5) is treated with chloromethyl octyl ether to synthesize a compound represented by general formula (6). [See Scheme 2.]

isopropylidene asiatic acid (11) is synthesized, which is then reacted under the condition described in Method 2, to synthesize a compound represented by general formula (12). [See Scheme 3.]

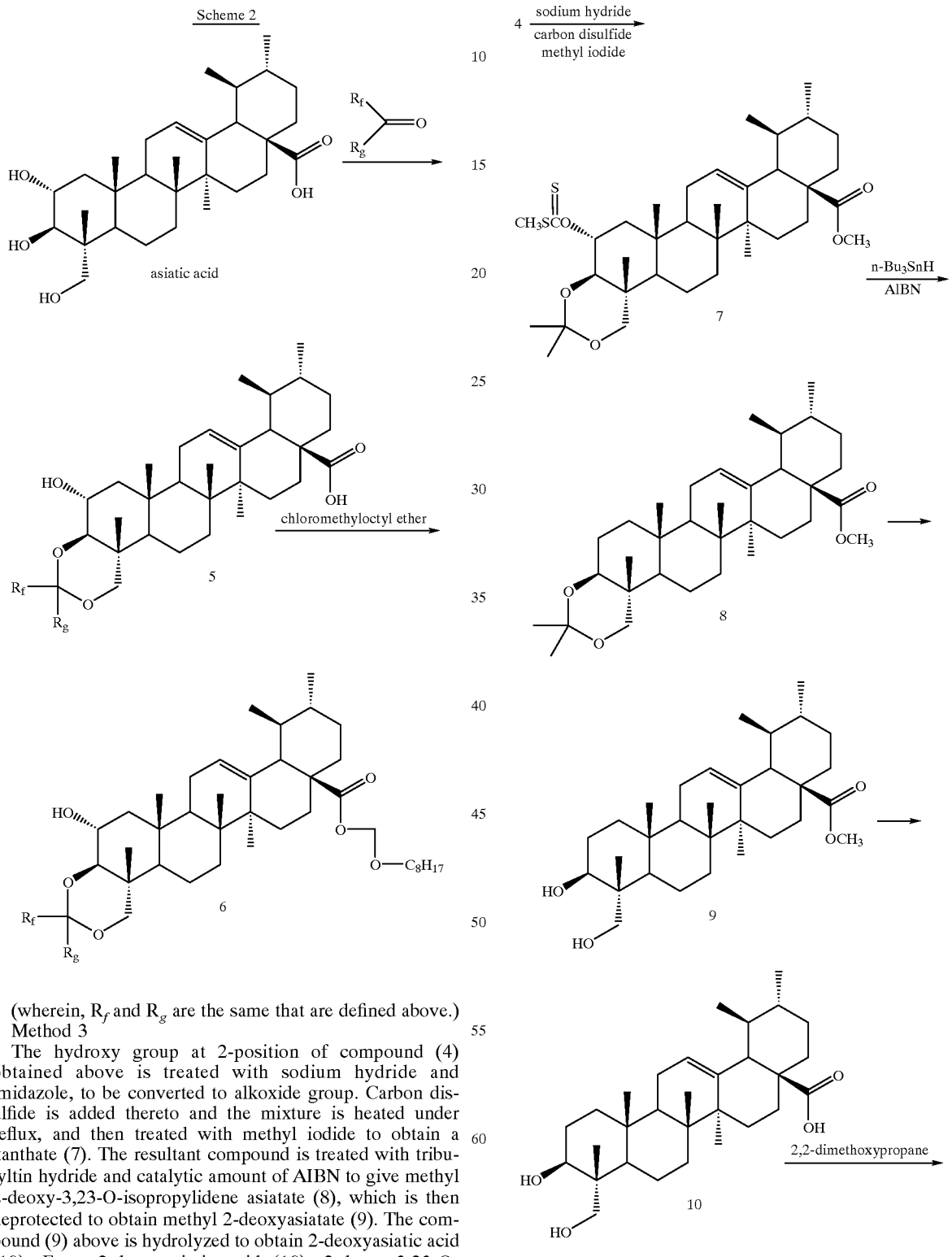

(wherein, $R_f$ and $R_g$ are the same that are defined above.)

Method 3

The hydroxy group at 2-position of compound (4) obtained above is treated with sodium hydride and imidazole, to be converted to alkoxide group. Carbon disulfide is added thereto and the mixture is heated under reflux, and then treated with methyl iodide to obtain a xanthate (7). The resultant compound is treated with tributyltin hydride and catalytic amount of AIBN to give methyl 2-deoxy-3,23-O-isopropylidene asiatate (8), which is then deprotected to obtain methyl 2-deoxyasiatate (9). The compound (9) above is hydrolyzed to obtain 2-deoxyasiatic acid (10). From 2-deoxyasiatic acid (10), 2-deoxy-3,23-O-

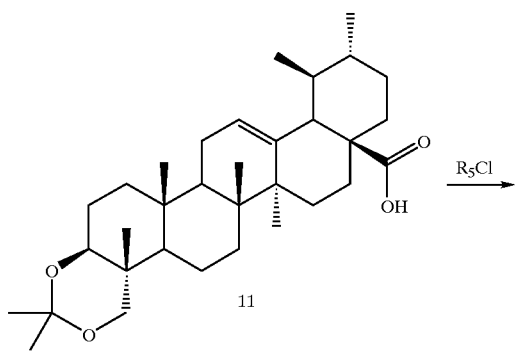

Method 4

Methyl 2-O-octyloxymethyl-3,23-O-isopropylidene asiatate (13) is synthesized by means of Method 2 from compound (4) obtained above. [See Scheme 4.]

Scheme 4

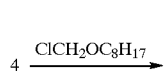

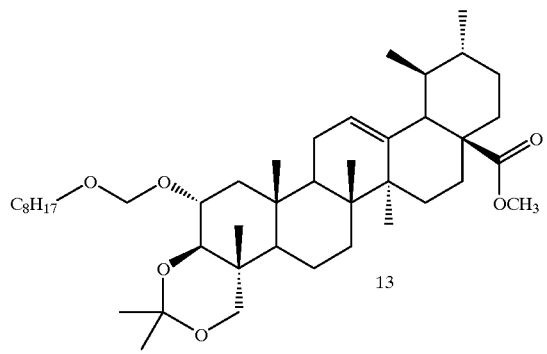

Method 5

The compound (3) obtained above is reacted with an alkyl halide under the conditions of Method 2, to synthesize a compound represented by general formula (14), which is acetylated at 2-position to synthesize a compound represented by general formula (15). [See Scheme 5.]

Scheme 5

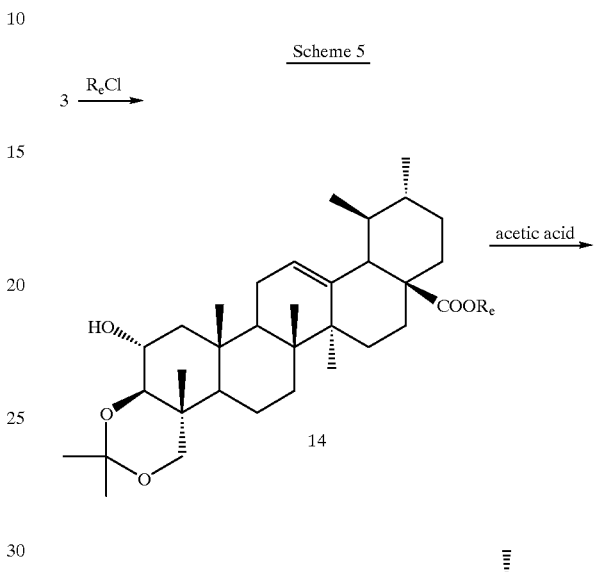

(wherein, $R_e$ is the same that is defined above.)

Method 6

From the compound (3) obtained above, ethoxymethyl 2-O-ethoxymethyl-3,23-O-isopropylidene asiatate (16) is obtained under the same conditions of Method 2 but with prolonged reaction time. By means of the same method, benzyloxymethyl group is incorporated to COOH group at 28-position by using chloromethyl benzyl ether. The resultant compound is acetylated to synthesize benzyloxymethyl 3,23-O-diacetylasiatate (17). [See Scheme 6.]

Scheme 6

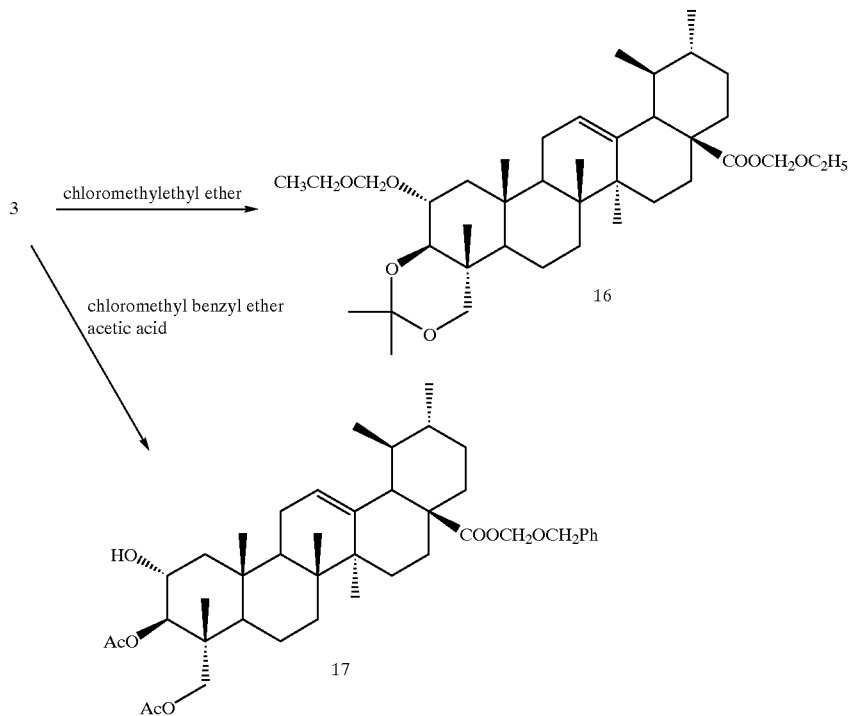

Method 7

2,3-Hydroxy group of asiatic acid is converted to 2,3-epoxy group, and the obtained compound is reacted with a variety of nucleophilic compound to cause ring opening of epoxy group to prepare a series of novel compounds according to the present invention. In other words, the compound (4) obtained above is reacted with methanesulfonyl chloride to obtain methyl 2-O-methanesulfonyl-3,23-O-isopropylidene asiatate (18), which is then treated with PTSA to give methyl 2-O-methanesulfonyl asiate (19). The obtained compound is then treated with potassium carbonate in methanol solvent to synthesize methyl 2,3-epoxyasiatate (20). The compound (20) is treated with lithium iodide trihydrate and acetic acid to synthesize methyl 2-α-iodo-2-deoxyasiatate (21) of which epoxide has been opened. [See Scheme 7.]

Scheme 7

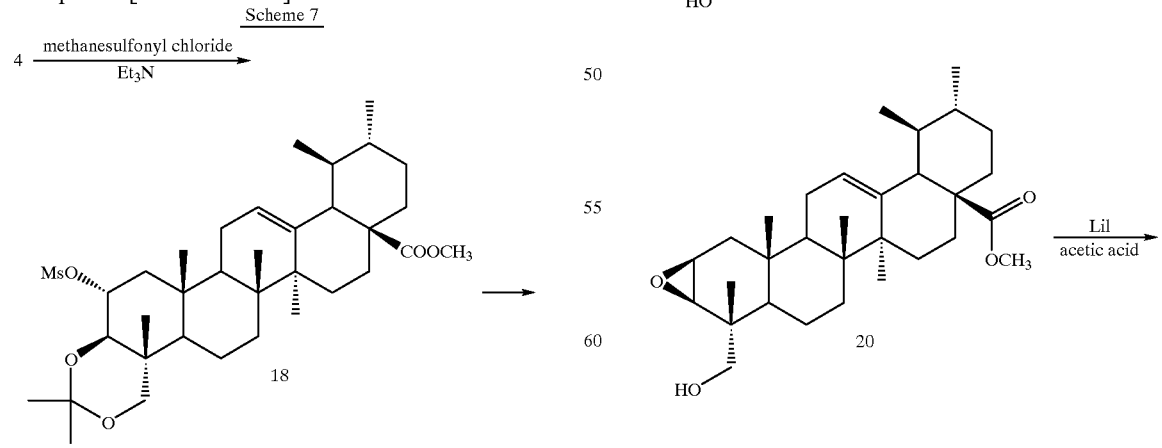

Method 8

Dihydroxy group at 3- and 23-position of asiatic acid was methylidene protected by dimethylsulfoxide and trimethylsilyl chloride to synthesize a compound represented by general formula (5, $R_f=R_g=H$), which is then treated with pyridinium dichromate (PDC) to obtain a compound represented by general formula (22). The resultant compound is reacted with chloromethyl octyl ether to give a compound represented by general formula (23). [See Scheme 8.]

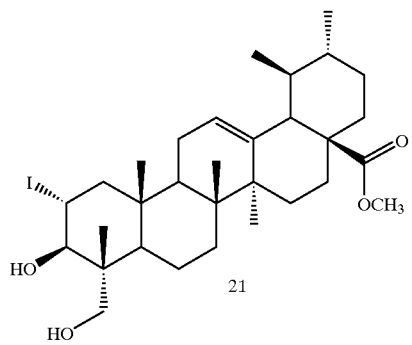

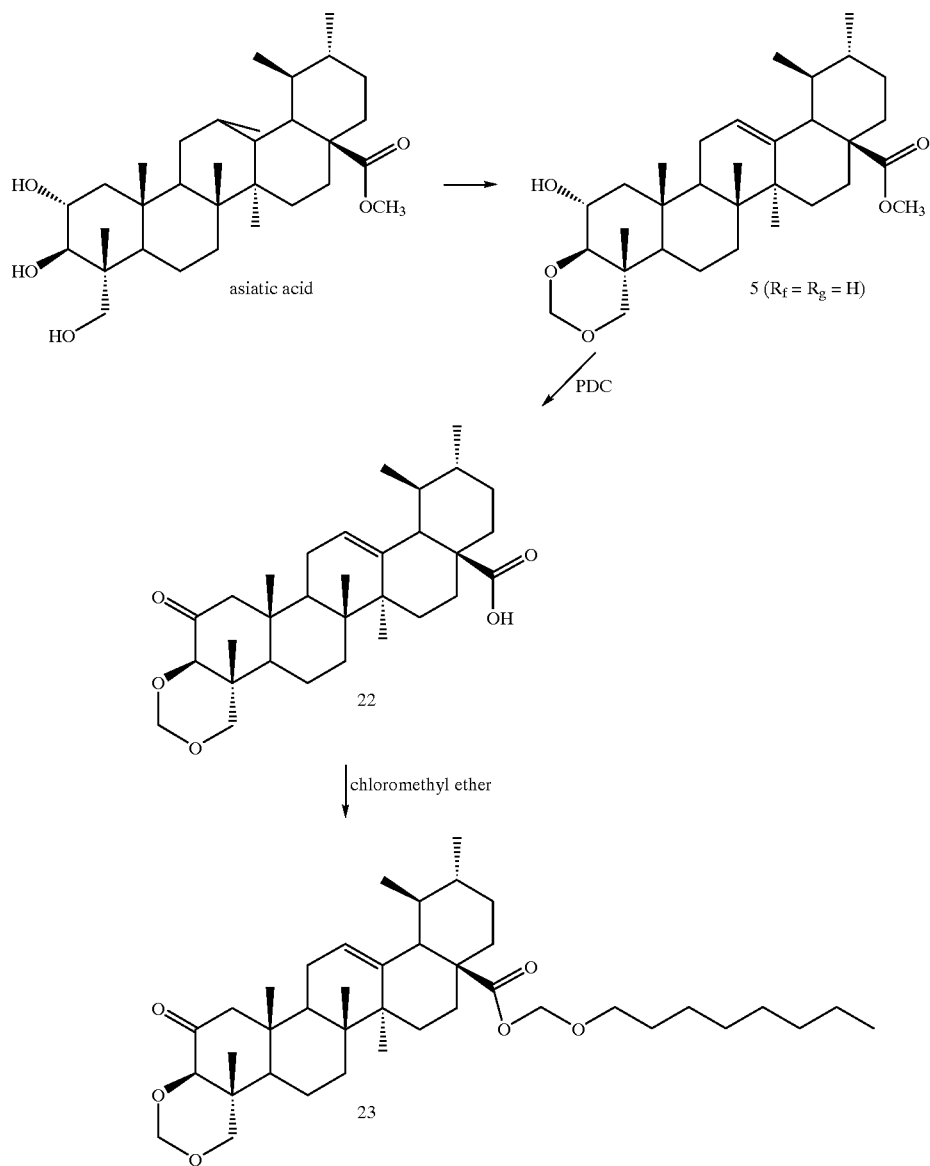

$LD_{50}$ value of mouse by injection of compounds according to present invention into abdominal cavity was 100~250 mg/kg the present invention, and that shows relative safety of compounds according to present invention.

The dose of compound of chemical formula (1) is 0.05 to 50 mg/day for an adult. The dose usually varies depending on age and body weight of a patient, as well as the condition of symptoms.

The medicines for treating dementia or cognitive disorder according to the present invention may be formulated into a suitable formulation for oral or parenteral administration by using conventional methods. For oral administration, it may be formulated as tablets, capsules, solution, syrup or suspension, while for parenteral administration, as transdermal or hypodermic injections, or injections into abdominal cavity or muscles.

BEST MODE FOR CARRYING OUT THE INVENTION

Now, the present invention is described with reference to Examples, Preparation Examples and Experimental Examples. However, it should be noted that the present invention is not restricted to those examples.

EXAMPLE 1

Isolation and purification of asiaticoside and asiatic acid in large scale

Quantitative extract (5 g) of *Centella asiatica* was directly separated by column chromatography (silica gel, 230–400 mesh; dichloromethane/methanol=10/1) to obtain asiatic acid (1.5 g), madecassic acid (1.4 g) and mixture (2.0 g) of asiaticoside and madecassoside. The obtained mixture was dissolved in minimum amount of 60% methanol, in a water bath at 100° C., and then cooled at room temperature to give pure asiaticoside as needle-like crystalline. (m.p.: 230–240° C.)

Separately, the extract (62 g) was dissolved in methanol (700 ml), and 5N sodium hydroxide solution(50 ml) was added thereto, and the resultant mixture was heated under reflux for 10 hours. The reaction mixture was concentrated under reduced pressure, neutralized, filtered and dried to obtain a mixture (2, 43 g) of asiatic acid and madecassic acid.

EXAMPLE 2

Preparation of 3,23-O-Isopropylidene asiatic acid (3)

The mixture (12 g) of asiatic acid and madecassic acid, and p-toluenesulfonic acid (200 mg) were dissolved in anhydrous DMF (100 ml), and 2,2-dimethoxypropane (5 ml) was added thereto by injection. The resultant mixture was stirred at room temperature for 14 hours, and then neutralized and concentrated under reduced pressure to remove the solvent. After extracting, washing and drying, the residue was purified by column chromatography (dichloromethane:methanol=30:1) to obtain 8.04 g of 3,23-O-isopropylidene asiatic acid (3).

IR (neat): 3440, 1698, 1200 $cm^{-1}$

Mass (EI): m/e 528 ($M^+$), 513 ($M^+$-Me), 482 ($M^+$-HCOOME), 452, 424, 407, 248, 203, 189, 133

$^1$H-NMR (CDCl$_3$): δ0.75, 1.04, 1.06, 1.09, 1.45, 1.46 (each s, 3H), 0.85 (d, 3H, J=6.4Hz), 0.95 (d, 3H, J=6.4Hz), 2.18 (d, 1H, J=11.2Hz), 3.32 (d, 1H, J=9.6Hz), 3.46, 3.51 (ABq, 2H, J=10.8Hz), 3.78 (m, 1H), 5.24 (brt, 1H)

EXAMPLE 3

Preparation of Methyl 3,23-O-isopropylideneasiatate (4)

3,23-O-Isopropylidene asiatic acid (3) (5 g) was dissolved in ethyl ether, and ethereal solution of diazomethane was slowly added dropwise thereto at 0° C. After stirring at room temperature for 1 hour, the reaction mixture was concentrated under reduced pressure to remove ether, and the residue was purified by column chromatography (hexane:ethyl acetate=3:1) to obtain 4.9 g of methyl 3,23-O-isopropylidene asiatate (4) (95%).

IR (neat): 3466, 1724, 1201 $cm^{-1}$

Mass (EI): m/e 542 ($M^+$), 527 ($M^+$-Me), 482 ($M^+$-HCOOME), 483, 467, 451, 407, 262, 203, 189, 133

$^1$H-NMR (CDCl$_3$): δ0.66, 0.97, 1.00, 1.02, 1.40, 1.39 (each s, 3H), 0.79 (d, 3H, J=6.4Hz), 0.87 (d, 3H, J=6.0Hz), 2.15 (d, 1H), 3.25 (d, 1H,J=9.6Hz), 3.41 3.43 (ABq, 2H), 3.53 (s, 3H), 3.72 (m, 1H), 5.18 (brt, 1H)

EXAMPLE 4

Preparation of 3,23-O-alkylidene asiatic acid (5)

① $R_f$=H, $R_g$=H

Dimethyl sulfoxide (2.5 eq.) and trimethylsilyl chloride (2.5 eq.) were added to THF with stirring. Asiatic acid (2) obtained above (2.53 g, 5.18 mmol) was added thereto, and the mixture was heated under reflux and argon atmosphere for 3 days. The solvent was evaporated under reduced pressure and the residue was purified by column chromatography (dichloromethane:methanol=20:1) to obtain 2.01 g of pale yellow solid (yield: 79.45%).

$^1$HNMR(300MHz,CDCl$_3$) δ0.75, 1.05, 1.08, 1.12(eachs, 3H), 0.85 (d, 3H, J=6.18Hz), 0.95 (d, 3H, J=5.76Hz), 2.19 (d, 1H, J=10.9Hz), 3.04, 3.76 (ABq, 2H, J=10.11Hz), 3.23 (d, 1H, J=10.23Hz), 3.87 (dt, 1H, J=4.26Hz, 10.02Hz), 4.95 (d,d, 2H, J=5.9Hz), 5.24 (t, 1H)

② $R_f$=H, $R_g$=CH$_3$

Asiatic acid (255 mg, 0.52 mmol) obtained above was dried over p-toluenesulfonic acid under reduced pressure. Then the compound was dissolved in anhydrous THF, and CH$_3$CH(OEt)$_2$ (0.15 ml) was added dropwise thereto, and the resultant mixture was stirred at room temperature for 2 hours. To the reaction mixture, saturated solution of sodium carbonate was added by injection, and the solvent was removed by evaporation under reduced pressure. The residue was diluted with ethyl acetate, washed and dried, and purified by column chromatography (dichloromethane:methanol=20:1) to obtain 178 mg of title compound (yield: 66.2%).

IR (neat) 2926, 1695 $cm^{-1}$

Mass (EI) m/e 514 [$M^+$]

$^1$H NMR (300MHz, CDCl$_3$) δ5.14 (t, 1H), 4.64 (qt, 1H, J=4.92Hz), 3.75 (m, 1H), 3.63, 2.97 (ABq, 2H, J=10.1Hz), 3.17 (d, 1H, J=10.4Hz), 0.98, 0.95, 0.65 (each s, 3H), 0.85 (d, 3H, J=5,49Hz), 0.75 (d, 3H, J=6.39Hz)

③ ($R_f$=H,$R_g$=C$_6$H$_5$

Excepting from substituting C$_6$H$_5$CH(OMe)$_2$ for CH$_3$CH(OEt)$_2$, the same procedure as Example 4② was performed (yield:32.1%).

IR (neat) 3437, 1696 $cm^{-1}$

Mass (EI) m/e 576 [$M^+$] 578

$^1$H NMR (300MHz, CDCl$_3$) δ7.52~7.49 (m, 2H), 7.37~7.35(m, 3H), 5.53(s, 1H), 5.24(t, 1H), 3.90, 3.30(ABq,

2H, J=10.11Hz), 3.47(d, 1H, J=10.47Hz), 2.18 (d, 1H, J=11.46Hz), 1.19, 1.09, 4.07, 0.77 (each s, 3H), 0.93 (d, 3H, J=6.09Hz), 0.85 (d, 3H, J=6.33Hz)

④ $R_f=CH_3, R_g=C_2H_5$

Excepting from substituting $C_2H_5COCH_3$ for $CH_3CH(OEt)_2$, the same procedure as Example 4② was performed (yield:58.96%).

IR (neat) 3436, 1694 cm$^{-1}$
Mass (EI) m/e 542 [M$^+$]
$^1$H NMR(300MHz, CDCl$_3$) δ5.18 (t, 1H), 3.68, 3.47 (ABq, 2H, J=4.26Hz), 3.48 (d, 1H, J=7.05Hz), 2.12(d, 1H,J=10.65Hz), 0.97, 0.89, 0.69 (each s, 3H)

⑤ $R_f=CH_3, R_g=C_3H_7$

Excepting from substituting $C_3H_7COCH_3$ for $CH_3CH(OEt)_2$, the same procedure as Example 4② was performed (yield:43.01%).

IR (neat) 3369, 2928, 1694 cm$^{-1}$
Mass (EI) m/e 558 [M$^+$+2]
$^1$H NMR(300MHz, CDCl$_3$) δ5.18 (t, 1H), 3.79~3.75 (m, 1H), 3.18 (d, 1H, J=10.23Hz), 3.67, 2.98 (ABq, 2H, J=9.8Hz), 2.12 (d, 1H, J=10.65Hz), 1.05, 1.01, 0.98, 0.69 (each s, 3H), 0.88 (d, 3H, J=5.55Hz), 0.79 (d, 3H, J=6.39Hz)

⑥ $R_fR_g=-(CH_2)_5-$

Excepting from substituting cyclohexanone for $CH_3CH(OEt)_2$, the same procedure as Example 4② was performed.

Mass (EI) m/e
$^1$H NMR (300MHz, CDCl$_3$) δ0.77, 0.96, 1.07 (each s, 3H), 0.85 (d, 3H, J=6.33Hz), 2.18 (d, 1H, J=11.46Hz), 3.24 (d, 1H, J=9.51Hz), 3.41, 3.59 (ABq, 2H, J=10.47Hz), 3.76 (dt, 1H, J=8.54Hz), 5.23 (t, 1H)

EXAMPLE 5

Preparation of octyloxymethyl 3, 23-O-alkylidene asiatate(6)

① $R_f=H, R_g=H$

The compound 5(258.4 mg, 0.52 mmol) obtained in Example 4① above was dissolved in anhydrous dichloromethane. Diisopropylethylamine (0.18 ml) was added thereto and stirred at room temperature for 10 minutes. At 0° C., chloromethyloctyl ether (0.1 ml) was added dropwise thereto and stirred for 5 minutes. Methanol was added thereto and the residue was refined by column chromatography (dichloromethane:methanol=30:1) to obtain 138 mg of white solid (yield: 41.6%).

$^1$H NMR (400MHz, CDCl$_3$) δ0.76, 1.05, 1.09, 1.13 (each s, 3H), 0.88 (d, 3H, J=5.6Hz), 0.95 (d, 3H, J=6.36Hz), 2.25 (d, 1H, J=10.8Hz), 3.04, 3.76 (ABq, 2H, J=10.0Hz), 3.22 (d, 1H, J=10.8Hz), 3.58 (m, 2H), 4.94 (d,d, 2H, J=6.0Hz), 5.21, 5.24 (ABq, 211, J=5.88Hz), 5.26 (t, 1H)

② $R_f=H, R_g=CH_3$

Excepting from substituting compound 5 obtained in Example 4② for compound 5 obtained in Example 4① above, the same procedure as Example 5① was performed.

IR (neat) 3481, 2927, 1732 cm$^{-1}$
Mass (EI) m/e 656 [M$^+$]
$^1$H NMR (300MHz, CDCl$_3$) δ5.22 (t, 1H), 5.20, 5.17 (ABq, 2H,J=6.21Hz), 4.69 (qt, 1H, J=4.95Hz), 3.84~3.77 (m, 1H), 3.69, 3.03(ABq, 2H, J=10.07Hz), 3.55 (m, 2H), 2.22 (d, 11H, J=11.16Hz), 1.05, 1.00, 0.95, 0.72 (each s, 3H), 0.84 (d, 3H, J=2.55Hz), 0.82 (d, 3H, J=2.19Hz)

③ $R_f=H, R_g=C_6H_5$

Excepting from substituting compound 5 obtained in Example 4③ for compound 5 obtained in Example 4① above, the same procedure as Example 5① was performed (yield;23.8%).

IR (neat) 3697, 1730 cm$^{-1}$
Mass (EI) m/e 719 [M$^+$+1]

④ $R_f=CH_3, R_g=C_2H_5$

Excepting from substituting compound 5 obtained in Example 4④ for compound 5 obtained in Example 4① above, the same procedure as Example 5① was performed (yield:58.96%).

IR (neat) 3469, 1733 cm$^{-1}$
Mass (EI) m/e 684 [M$^+$]
$^1$HNMR(300MHz,CDCl$_3$) δ5.16(t, 1H),5.14, 5.11 (ABq, 2H, J=6.29Hz), 3.68(m,1H), 3.48 (m, 2H,), 3.24 (d, 1H, J=9.57Hz), 2.16(d, 1H,J=11.5Hz), 1.00, 0.96, 0.91, 0.66 (each s, 3H), 0.84(d,1H,J=5.55Hz), 0.76(d,1H,J=5.73Hz)

⑤ $R_f=CH_3, R_g=C_3H_7$

Excepting from substituting compound 5 obtained in Example 4⑤ for compound 5 obtained in Example 4① above, the same procedure as Example 5① was performed (yield:80.2%).

IR (neat) 3468, 2927, 1729 cm$^{-1}$
Mass (EI) m/e 698 [M$^+$]
$^1$H NMR (400MHz, CDCl$_3$) δ5.26~5.20 (m, 2H), 5.10 (t, 1H), 3.87~3.84 (m, 1H), 3.60~3.56 (m, 2H), 2.27 (d, 1H), 1.08, 1.07, 1.03, 0.76 (each s, 3H), 0.94 (d, 3H, J=5.84Hz), 0.87 (d, 3H, J=5.4Hz)

⑥ $R_fR_g=-(CH_2)_5-$

Excepting from substituting compound 5 obtained in Example 4⑥ for compound 5 obtained in Example 4① above, the same procedure as Example 5① was performed (yield: 34%).

Mass (EI) m/e 710 [M$^+$], 667, 596, 567, 522, 521
$^1$H NMR (400MHz, CDCl$_3$) δ0.75, 0.95, 1.03 (each s, 3H), 0.87 (d, 3H, J=5.86Hz), 1.09 (d, 3H, J=3.9Hz), 2.10 (d, 1H, J=4.40Hz), 3.35 (d, 1H, J=9.77Hz), 3.48, 3.52 (ABq, 2H, J=1 1.24Hz), 3.58 (m, 2H), 3.8 (m, 1H), 5.21, 5.24 (dd, 2H, J=5.86Hz), 5.26 (t, 1H)

EXAMPLE 6

Preparation of methyl 3, 23-O-isopropylidene-2-O-[(methylthio)thiocarbonyl]asiatate(7)

Sodium hydride(60% dispersion of inorganic oil, 18.3 mg, 0.46 mmole), imidazole(2 mg) and tetrahydrofuran(2 ml) were added to methyl 3,23-O-isopropylidene asiatate (4) (50 mg, 0.092 mmole) and the resultant mixture was stirred for 30 minutes. Carbon disulfide(0.2 ml, excessive amount) was added thereto and refluxed for 2 hours. Methyl iodide (0.1 ml, excessive amount) was added thereto and heated under reflux again for 1 hour. The reactant mixture was treated with water and the solvent was removed under reduced pressure. After extracting, washing and drying the residue was refined by column chromatography (hexane:ethyl acetate=10:1) to obtain 56 mg of white solid (yield: 96%).

IR (neat): 1723, 1233, 1057 cm$^{-1}$
$^1$H NMR (CDCl$_3$) δ5.78(1H,m), 5.24(1H,bt), 3.80(1H,d, J=10Hz), 3.60(3H,s), 3.54, 3.58(2H,dd,J=7.2Hz), 2.51(3H, s), 2.23(1H,d,J=11.2Hz), 0.94(3H,d, J=5.2Hz), 0.84(3H,d, J=6Hz), 0.73, 1.09, 1.11, 1.14, 1.41, 1.45 (each 3H,s).

EXAMPLE 7

Preparation of methyl 2-deoxy-3, 23-O-isopropylidene asiatate(8)

A catalytic amount of AIBN and benzene(10 ml) were added to xanthate compound (7)(202 mg, 0.32 mmole)

obtained above. Tributyltin hydride(0.26 ml, 0.96 mmole) was added thereto with the resultant heated under reflux and stirred for 1 hour and a half. The reactant mixture was concentrated under reduced pressure and the solvent was removed. The obtained residue was refined by column chromatography(hexane:ethyl acetate=10:1) to obtain 168 mg of white solid (yield: 100%). The product was recrystallized with hexane to yield needle-like crystalline.

IR (neat): 1724 cm$^{-1}$

MS (EI): 527(M$^+$+1), 512, 407, 262, 203, 133.

$^1$H NMR (CDCl$_3$) δ5.25(1H,bt), 3.60(3H,s), 3.52(1H,t), 3.44, 3.54(2H,dd,J=10Hz), 2.23(1H,d,J=11.2Hz), 0.94 (3H, d, J=5.6Hz), 0.86(3H,d,J=6.4Hz), 0.73, 0.97, 1.07, 1.09, 1.42, 1.45(each 3H,s)

EXAMPLE 8

Preparation of methyl 2-deoxyasiatate(9)

Tetrahydrofuran(10 ml) and 1N HCl solution(1 ml) were added to compound(8) (460 mg, 0.87 mmole) obtained above and stirred at room temperature for 5 hours. The solvent was totally removed by distillation under reduced pressure. The obtained residue was refined by column chromatography(hexane:ethyl acetate=3:2) to obtain 402 mg of white solid (yield: 95%). The crude product obtained was recrystallized with ethyl acetate to yield needle-like crystalline.

IR (neat): 3400, 1724 cm$^{-1}$

MS (EI): 486(M$^+$), 426, 262, 203, 133

EXAMPLE 9

Preparation of 2-deoxyasiatic acid (10)

LiI-3H$_2$O (450 mg, 2.39 mmole) and 2,4,6-colidine(5 ml) was added to methyl 2-deoxyasiatate (9) (38 mg, 0.78 mmole) and heated under reflux for 10 hours. The flask was covered with aluminium foil to block light during reflux. The reactant solution was concentrated under reduced pressure to remove collidine. The obtained residue was refined by column chromatography(dichloromethane:methanol= 20:1) to obtain pale yellow solid (yield : 99%). The product obtained was recrystallized with methanol to yield 280 mg of needle-like crystalline(yield: 76%).

IR (KBr): 3436, 1693 cm$^{-1}$

MS (EI): 472(M$^+$) 426, 248, 203, 133

$^1$H NMR (CDCl$_3$+pyridine-d$_5$) δ5.21(1H,bt,J=2.8Hz, 3.6Hz), 3.60(1 H,t,J=7.2Hz, 8.2Hz), 3.3 6, 3.70 (2H,dd,J= 10.0Hz), 2.21(1H,d,J=11.2Hz).

EXAMPLE 10

Preparation of 2-deoxy-3, 23-O-isopropylidene asiatic acid (11)

Excepting from substituting compound 10 for the mixture of asiatic acid and madecassic acid, the same procedure as Example 2 was performed (yield:59.9%).

IR (neat) 2928, 1697 cm$^{-1}$ $^1$H NMR (400MHz, CDCl$_3$) δ5.25 (d,1H),3.52 (t,1H), 2.17 (d,1H), 1.44, 1.40, 1.10, 1.04, 0.98, 0.78 (each s, 3H), 0.95 (d, 3H, J=6.4Hz), 0.87 (d, 3H, J=6.4Hz)

EXAMPLE 11

Preparation of octyloxymethyl 2-deoxy-3, 23-O-isopropylidene asiatate(12, R$_e$=octyloxymethyl)

Excepting from substituting compound 11 for compound 5 in Example 5①above, the same procedure as Example 5① was performed (yield:53.9%).

IR (neat) 2929, 1733 cm$^{-1}$

Mass (EI) m/e 654 [M$^+$]

$^1$H NMR (500MHz, CDCl$_3$) δ5.17 (t, 1H), 5.14, 5.12 (ABq, 2H, J=6.02Hz), 3.49~3.48 (m, 2H), 3.46, 3.34(ABq, 2H,J=6.17Hz), 2.15 (d, 1H), 1.35, 1.32, 1.01, 0.96, 0.67 (each s, 3H), 0.87 (d, 3H, J=7.04Hz),

EXAMPLE 12

Preparation of ethyloxymethyl 2-deoxy-3, 23-O-isopropylidene asiatate(12, R$_e$=ethoxymethyl)

Excepting from substituting compound 11 for compound 5 in Example 5① and substituting chloromethylethyl ether for chloromethyloctyl ether, the same procedure as Example 5① was performed (yield:46%).

IR (neat) 2929, 1733 cm$^{-1}$

Mass (EI) m/e 570 [M$^+$]

$^1$H NMR (500MHz, CDCl$_3$) δ5.16 (t, 1H), 5.16 (s, 2H), 3.60, 3.58(ABq, 2H, J=1.36Hz), 3.45~3.35 (m, 3H), 2.15 (d, 1H), 1.45, 1.38, 1.34, 1.04, 0.98, 0.70 (each s, 3H), 0.88 (d, 3H, J=6.32Hz), 0.79 (d, 3H, J=2.24Hz)

EXAMPLE 13

Preparation of tetrahydropyranyl 2-deoxy-3, 23-O-isopropylidene asiatate (12, R$_e$=2-tetrahydropyranyl)

Compound 11(133 mg, 0.26 mmol) and pyridinium para-toluene sulfonate(catalytic amount) were dissolved in anhydrous dichloromethane. Dihydropyrane(0.07 ml) was added dropwise thereto and stirred at room temperature for 40 hours. The resultant was neutralized and the solvent was removed under reduced pressure. After extracting, washing and drying, the residue was refined by column chromatography (hexane:ethyl acetate=8:1) to 73 mg of compound(12, R$_e$=2-tetrahydropyranyl) (yield:47.2%).

IR (neat) 2945, 1733 cm$^{-1}$ $^1$H NMR (400MHz, CDCl$_3$) δ5.96(t, ½H), 5.92(t, ½H), 5.28(t, ½H), 5.26 (t, ½H), 3.88 (t, 1H), 3.67 (t, 1H), 3.52 (t, 2H), 3.46 (t, 2H), 1.45, 1.42, 1.11, 1.05, 0.96 (each s, 3H), 0.87 (d, 3H, J=6.4Hz)

EXAMPLE 14

Preparation of methyl 2-O-octyloxymethyl-3,23-O-isopropylidene asiatate (13)

Excepting from substituting compound 4 for compound 5 in Example 5①, the same procedure as Example 5① was performed.

IR (neat) 2927, 1728 cm$^{-1}$

Mass (EI) m/e 684 [M$^+$]

$^1$H NMR(500MHz, CDCl$_3$) δ5.18(t, 1H),4.73, 4.62 (ABq, 2H, J=6.72Hz), 3.70~3,65 (m, 1H), 3.53 (s, 3H), 3.35 (d, 1H, J=9.76Hz), 1.36, 1.33, 1.02, 1.01, 0.96, 0.66 (each s, 3H), 0.87 (d, 3H, J=6.18Hz), 0.79 (d, 3H, J=6.46Hz)

EXAMPLE 15

Preparation of methoxymethyl 3, 23-O-isopropylidene asiatate (14, R$_e$=methoxymethyl)

Excepting from substituting compound 3 for compound 5 in Example 5① and substituting chloromethylmethyl ether for chloromethyloctyl ether, the same procedure as Example 5① was performed (yield: 19%).

mp. 104–112° C.

$^1$H NMR(300MHz, CDCl$_3$): δ0.77, 1.04, 1.08, 1.11, 1.45, 1.46(each s, 3H), 0.87 (d, 3H, J=6.3Hz), 0.96(d, 3H, J=5.7Hz), 2.27 (d, 1H, J=11.1Hz), 3.32 (d, 1H, J=9.6Hz), 3.45 (s, 3H), 3.47 (d, 1H, 9.6Hz), 3.55 (d, 1H, 9Hz), 3.79 (m, 1H), 5.17 (d, 1H, 6Hz), 5.20 (d, 2H, J=6Hz), 5.28 (t, 1H, J=3.5Hz)

IR (KBr) cm$^{-1}$ 3500, 2950, 1740, 1450, 1380, 1065, 925, 860

$[\alpha]_o^{23}$ =+10.4° (c=0.2, CHCl$_3$)

EXAMPLE 16

Preparation of ethoxymethyl 3, 23-O-isopropylidene asiatate (14, R$_e$=ethoxymethyl)

Excepting from substituting compound 3 for compound 5 in Example 5①  and substituting chloromethylethyl ether for chloromethyloctyl ether, the same procedure as Example 5① was performed (yield:46%).

IR (neat): 3468, 1734 cm$^{-1}$

MS (EI) m/z: 586 (M$^+$)

$^1$H NMR (400 MHz, CDCl$_3$) δ5.27 (t,1H), 5.23 (s,2H), 3.74–3.82 (m,1H), 3.66 (q,2H,J=7.6Hz), 3.53, 3.44 (ABq, 2H), 3.32 (d, 1H, J=9.6Hz), 2.25 (d, 1H), 1.46, 1.44, 1.10 (ABq, 2H), 1.07, 1.03, 0.76 (each s, 3H), 1.22 (t, 3H, J=6.8Hz), 0.95 (d, 3H, J=5.6Hz), 0.86 (d, 3H, J=6.4Hz)

EXAMPLE 17

Preparation of methoxyethoxymethyl 3, 23-O-isopropylidene asiatate (14, R$_e$=methoxyethoxymethyl)

Excepting from substituting compound 3 for compound 5 in Example 5① and substituting methoxyethoxymethyl chloride for chloromethyloctyl ether, the same procedure as Example 5① was performed (yield:25%).

mp. 76–79° C.

$^1$H NMR(300MHz, CDCl$_3$): δ0.77, 1.04, 1.08, 1.11, 1.45, 1.46 (each s, 3H), 0.86 (d, 6.3Hz, J=3Hz), 0.96 (d, 3H, J=5.7Hz), 2.2–0.9 (m, 21H), 2.26 (d, 1H, J=10.2Hz), 3.32 (d, 1H, J=9.6Hz), 3.39 (s, 3H), 3.47 (d, J=9.0Hz), 3.52 (d, 1H, J=9.0Hz), 3.55 (t, 2H, J=5.1Hz), 3.77 (m, 1H), 3.77 (t, 2H, J=5.1Hz), 5.26 (t, 1H, J=3.6Hz), 5.28 (s, 2H)

IR (KBr) cm$^{-1}$ 3500, 2950, 1725, 1450, 1380, 1070, 940, 860

$[\alpha]_o^2$=+38.7° (c=0.1, CHCl$_3$)

EXAMPLE 18

Preparation of methoxymethyl 2-O-acetyl-3, 23-O-isopropylideneasiatate(15, R$_e$=methoxymethyl)

Compound(14)(R$_5$=methoxymethyl, 139 mg, 0.24 mmol) obtained above was dissolved in pyridine and stirred. Acetic anhydride(0.04 ml, 0.38 mmol) was added thereto and stirred for 2 days. The resultant was concentrated under reduced pressure, washed, dried and refined by column chromatography (dichloromethane:methanol=30:1) to 75 mg of white solid (yield:52%).

mp. 110–115° C.

$^1$H NMR (300MHz,CDCl$_3$): δ0.77, 1.09, 1.11, 1.12, 1.41, 1.43, 2.01 (each s, 3H), 0.86 (d, 3H, J=6.3Hz), 0.95 (d, 3H, J=6Hz), 2.27 (d, 1H, J=10.8Hz), 3.45 (s, 3H), 3.50 (d, 1H, J=9.6Hz), 3.52 (d, 1H, J=9.6Hz), 3.56 (d, 3H, J=9Hz), 5.0 (m, 1H), 5.17 (d, 1H, J=6Hz), 5.20 (d, 1H, J=6Hz), 5.27 (t, 1H, J=3.5Hz)

IR (KBr) cm$^{-1}$ 2950, 2740, 1450, 1240, 1080, 1025, 950, 800

$[\alpha]_o^{24}$=+43.6° (c=0.1, CHCl$_3$)

EXAMPLE 19

Preparation of ethoxymethyl 2-O-acetyl-3, 23-O-isopropylideneasiatate(15, R$_e$=ethoxymethyl)

Excepting from substituting compound 14 (R$_5$=ethoxymethyl) obtained for compound 14 (R$_5$=methoxymethyl) used in Example 18, the same procedure as Example 18 was performed (yield:91%).

mp. 136–137° C.

$^1$H NMR (300MHz, CDCl$_3$): δ0.85 (d, 3H, J=6.1Hz), 0.95 (d, 3H, J=5.7Hz), 1.01, 1.06, 1.08, 1.41, 1.43, 2.01 (each s, 3H), 0.9–2.2 (m, 20H), 1.21 (t, 7.3Hz), 2.26 (d, 1H, 11.1Hz), 3.48 (d, 1H, J=9Hz), 3.53 (d, 1H, J=9Hz), 3.54 (d, 1H, J=10.7Hz), 3.66 (q, 2H, J=7.3Hz), 5.00 (dt, 1H, 4.3, 10.7Hz), 5.23 (s, 2H), 5.26 (t, 1H, J=4.2Hz)

$[\alpha]_o^{24}$=−0.66° (c=0.34, CCl$_4$)

EXAMPLE 20

Preparation of ethoxymethyl 2-O-ethoxymethyl-3, 23-O-isopropylideneasiatate (16)

Excepting from substituting compound 3 for compound 5 obtained in Example 5① above, and substituting chloromethylethyl ether for chloromethyloctyl ether, the same procedure as Example 5① was performed (yield: 19%).

mp. 68–70° C.

$^1$H NMR (300MHz, CDCl$_3$): δ0.86 (d, 3H, J=6.3Hz), 0.95 (d, 3H, J=5.7Hz), 0.80, 1.05, 1.10, 1.41, 1.51 (each s, 3H), 0.9–2.2 (m, 20H), 1.22 (t, 3H, J=7.2Hz), 2.26 (d, 1H, J=11.1 Hz), 3.35 (d, 1H, J=9Hz), 3.39 (d, 1H, J=9Hz), 3.46 (d, 1H, J=9.6Hz), 3.60 (q, 2H, J=7.2Hz), 3.76 (q, 2H, J=7.2Hz), 3.80 (dt, 1H, 4.2, 9.6Hz), 4.67 (s, 2H), 5.24 (s, 2H), 5.27 (t, 1H, J=3.6Hz)

IR (KBr) cm$^{-1}$ 2950, 1715, 1450, 1380, 1020, 925, 860

$[\alpha]_o^{24}$=+33.1° (c=0.1, CHCl$_3$)

EXAMPLE 21

Preparation of benzyloxymethyl 3, 23-O-diacetyl asiatate (17)

Excepting from substituting compound 3 for compound 5 obtained in Example 5① and substituting chloromethylbenzyl ether for chloromethyloctyl ether, the same procedure as Example 5① was performed and then synthesized through acetylization (yield:45%).

$^1$H NMR (300MHz, CDCl$_3$): δ0.75, 0.85, 0.99, 1.10, 2.04, 2.09 (each s, 3H), 0.89 (d, 3H, J=6.3Hz), 0.9–2.2 (m, 21H), 2.27 (d, 1H, J=12.9Hz), 3.57 (d, J=11.7Hz), 3.83 (d, J=11.7Hz), 3.90 (dt, 1H, 3.9, 10.2Hz), 4.68 (s, 2H), 5.04 (d, 1H, J=10.2Hz), 5.28 (t, 1H, J=3.6Hz), 5.32 (s, 3H), 7.34 (s, 5H)

IR (neat) cm$^{-1}$ 2950, 2740, 1450, 1380, 1065, 925, 860, 800

$[\alpha]_o^{25}$=+25.25° (c=0.1, CHCl$_3$)

EXAMPLE 22

Preparation of methyl 2-O-methanesulfonyl-3, 23-O-isopropylideneasiatate (18)

Methyl 3, 23-O-isopropylidene asiatic acid (4) (354.7 mg, 0.65 mmole) was dissolved in dichloromethane(15 ml).

Triethyl amine(82.4 mg, 0.72 mmole) and methanesulfonyl chloride(99.2 mg, 0.98 mmole) were added thereto and stirred at 0° C. for 3 hours under nitrogen atmosphere. After the reaction was finished, the solvent was removed. After extracting, washing and drying, the residue was refined by column chromatography (hexane:ethyl acetate=2:1) to 380 mg of pure compound (18) as white solid (yield:93%).

$^1$H NMR (CDCl$_3$) δ5.24(1H, m), 4.69–4.62 (1H, m), 3.60 (3H, s), 3.57 (1H, d, J=10.5Hz), 3.53 (1H, d, J=10.5Hz), 3.49 (1H, d, J=10.5Hz), 3.01 (3H, s), 2.26–2.20 (1H, m), 2.23(1H, bs), 1.44 (3H, s), 1.40 (3H, s), 1.11 (3H, s), 1.09 (3H, s), 1.07 (3H, s), 0.94 (3H, d, J=6.0Hz), 0.85 (3H, d, J=7.0Hz), 0.72(3H,s)

EXAMPLE 23

Preparation of methyl 2-O-methanesulfonyl asiatate (19)

The compound(18) (1.2 g, 1.92 mmole) obtained above was dissolved in methanol(30 ml). p-toluenesulfonic acid (480 mg, 2.52 mmole) was added thereto and refluxed for 10 minutes under nitrogen atmosphere. The reactant was neutralized, extracted, washed, dried and refined by column chromatography (hexane:ethyl acetate=1:1) to obtain 1.06 g of pure compound (19) as colorless oil(yield: 94%).

$^1$H NMR (CDCl$_3$) δ5.24 (1H, m), 4.77–4.74 (1H, m), 3.69 (1H, d, J=10.5Hz), 3.61 (3H,s), 3.44 (1H, d, J=10.5Hz), 3.70 (1H, bs), 3.10 (3H, s), 1.08 (3H, s), 1.07 (3H, s), 0.95 (3H, s), 0.94 (3H, d, J=5.1Hz), 0.85 (3H, d, J=6.5Hz), 0.74 (3H, s)

EXAMPLE 24

Preparation of methyl 2,3-epoxyasiatate (20)

The compound(19) (2.78 g, 4.77 mmole) obtained above was dissolved in methanol(60 ml). Potassium carbonate (1.32 g, 9.53 mmole) was added thereto and stirred at room temperature for 3 days under nitrogen atmosphere. After the reaction was finished, solvent was removed. After extracting, washing and drying, the residue was refined by column chromatography (hexane : ethyl acetate=2: 1) to obtain 2.05 g of pure compound (20) as white solid (yield: 89%).

m.p.: 230~234° C.

IR (KBr): 3400, 2920, 1730, 1430, 1450, 1200, 1040 cm$^{-1}$ $^1$H NMR (CDCl$_3$) δ5.27 (1H, m), 3.60 (3H, s), 3.56 (1H, m), 3.31 (1H, m), 3.27 (1H,m), 3.11 (1H, d, J=4.0Hz), 1.12 (3H, s), 1.6 (3H, s), 0.96 (3H, s), 0.94 (3H, d, J=5.1Hz), 0.86 (3H, d, J=6.4Hz), 0.74 (3H, s)

EXAMPLE 25

Preparation of methyl 2β-iodo-2-deoxyasiatate(21)

Compound 20(24.5 mg, 0.05 mmol), LiI·3H$_2$O (98 mg, 10.3 eq) were dissolved in THF(5 ml). AcOH(0.5 ml) was added thereto with stirring, and the resultant was reacted for 1 day under argon atmosphere. The resultant was diluted with water, extracted with ethyl acetate, washed with brine and 10% Na$_2$S$_2$O$_3$ solution, dried, and refined by column chromatography(hexane:ethyl acetate=3:1) to obtain 16.5 mg of colorless solid (yield: 53.3%).

$^1$H NMR(300MHz, CDCl$_3$): δ0.74, 0.85, 1.02, 1.08 (each s, 3H), 0.86 (d, 3H, J=6.3Hz), 0.94 (d, 3H, J=5.13Hz), 2.24 (d, 1H, J=11.2Hz), 3.42, 3.72 (ABq, 2H, J=12.7Hz), 3.60 (s, 3H), 4.57 (dt, 1H), 5.25 (t, 1H)

Mass (EI) m/e 612 [M$^+$], 552, 467, 407, 349

EXAMPLE 26

Preparation of 3,23-O-metbylidene-2-oxoasatic acid (22)

Compound 5(R$_f$=R$_g$=H, 1.1 g 2.2 mmole) and pyridinium dichromate(0.83 g, 2.2 mmole) were dissolved in anhydrous dichloromethane. Acetic anhydride (0.62 ml) was added thereto and heated under reflux for 2 hours. The reactant was diluted with ethyl acetate, filtrated and refined by column chromatography (dichloromethane:methanol= 20:1) to obtain compound 23(0.32 g, yield 29.2%)

$^1$H NMR (300MHz, CDCl$_3$) δ0.75, 1.02, 1.07, 1.13 (each s, 3H), 0.95 (d, 3H, J=5.9Hz), 0.85 (d, 3H, J=6.3Hz), 2.11–2.21 (m, 2H), 2.39 (d, 1H, J=12.7Hz), 3.42, 3.84 (ABq, 2H, J=10.4Hz), 4.10 (s, 1H), 4.69, 5.20 (ABq, 2H, J=5.9Hz), 5.23 (t, 1H)

EXAMPLE 27

Preparation of Octyloxymethyl 3,23-O-methylidene-2-oxoasiatate(23)

Except from substituting compound 22 for compound 5 used in Example 5①, the same procedure as Example 5① was performed(yield: 44%).

$^1$H NMR (300MHz, CDCl$_3$) δ0.78, 1.02, 1.10, 1.14 (each s, 3H), 0.87 (d, 3H, J=7.3Hz), 0.95 (d, 3H, J=5.9Hz), 2.13, 2.40 (ABq, 2H, J=12.7Hz), 2.27 (d, 1H, J=11.5Hz), 3.42, 3.84 (ABq, 2H, J=10.1Hz), 3.58 (dt, 2H, J=5.6Hz), 4.10 (s, 1H), 4.69, 5.24 (ABq, 2H, J=6.1Hz), 5.20–5.25 (m, 2H), 5.25 (t, 1H)

PREPARATION EXAMPLE 1

Tablets

| | |
|---|---|
| Active component | 2.5 mg |
| Lactose BP | 151.0 mg |
| Starch BP | 30.0 mg |
| Pre-gelatinized corn starch BP | 15.0 mg |

The active component was sieved, and mixed with lactose, starch and pre-gelatinized corn starch. Suitable amount of purified water was added thereto and the mixture was granulated. After drying, the granules were mixed with magnesium stearate and pressed to prepare tablets.

PREPARATION EXAMPLE 2

Capsules

| | |
|---|---|
| Active component | 2.5 mg |
| Starch 1500 | 96.5 mg |
| Magnesium stearate BP | 1.0 mg |

The active component was sieved and mixed with vehicles. The mixture was filled in gelatin capsules.

PREPARATION EXAMPLE 3

Injections

| Active component | 800 µg/ml |
|---|---|
| Dilute hydrochloric acid BP | until pH 3.5 |
| Injectable sodium chloride BP | maximum 1 ml |

Active component was dissolved in proper amount of injectable sodium chloride BP, and the pH of the resultant solution was adjusted to 3.5 by adding dilute hydrochloric acid BP. Then the volume of the solution was adjusted by using injectable sodium chloride BP, and the solution was thoroughly mixed. The solution was charged into 5 ml type 1 ampoule made of transparent glass, and the ampoule was sealed under the upper lattice of air, by fusing the glass. Then the ampoule was sterilized by autoclaving at 120° C. for 15 minutes or more, to give injection.

EXPERIMENTAL EXAMPLE 1

Effect of asiatic acid derivatives on treating dementia induced by scopolamine

On a male ICR mouse having body weight of 25–30 g, dementia was induced by subcutaneous injection of 1 mg/kg of scopolamine, 30 minutes before the experiment.

The compound according to the present invention was injected into abdominal cavity, and after 1 hour, scopolamine (1 mg/kg) was subcutaneously injected. After 30 minutes, passive avoidance was measured in order to examine anti-dementia effect of the compound to prevent dementia induced by scopolamine. As control groups, animals without administration of scopolamine and animals with administration of scopolamine were observed. Animals with administration of asiatic acid and Velnacrine, which has been already used as an anti-dementia agent were used as a comparative example.

Passive avoidance test was carried out as follows:

An avoidance shuttle box (40×20×20 cm) having lattices of 3 mm thickness in an interval of 0.5 cm at the bottom was divided into a light room and a dark room. A mouse was placed in the bright room, and when it entered into the dark room, training was given by causing electric stimulus of 0.3 mA to the mouse by the use of a grid. After 24 hours, same experiment was performed, and the retention time of the mouse in the bright room was measured to make an index of remembering the training of the day before. Retention time of 180 seconds or more is evaluated as "positive".

In order to exhibit the anti-dementia effect, the retention time (180 sec) of a normal mouse without inducing dementia in the bright room was set to 100%, while the retention time (34.5 sec) of a mouse having dementia induced by scopolamine in the light room was set to 0%.

The experimental results are shown in Table 1 below:

TABLE 1

Anti-dementia effect of asiatic acid derivatives on dementia induced by scopolamine

| Compound | Concentration (mg/kg) | Retention time (sec) | anti-dementia effect (%) |
|---|---|---|---|
| asiatic acid | 0.1 | 23.1 ± 11.2 | −7.8 |
|  | 1.0 | 55.5 ± 21.9 | 14.4 |
| Velnacrine | 1.0 | 92.7 ± 19.2 | 40.0 |
| 2-oxoasiatic acid | 0.1 | 36.2 ± 18.8 | 5.5 |
|  | 1.0 | 145.5 ± 24.7 | 75.4 |
| octyloxymethyl 3β, 23-dihydroxyurs-12-en-28-oate | 0.1 | 42.5 ± 8.2 | 5.5 |
|  | 1.0 | 63.9 ± 23.3 | 20.2 |
| Methyl 3,23-O-isopropyliden-2-oxoasiatate | 0.1 | 65.8 ± 21.1 | 21.5 |
|  | 1.0 | 49.2 ± 15.9 | 10.1 |
| Methyl 2-oxoasiatate | 0.1 | 44.2 ± 8.9 | 6.7 |
|  | 1.0 | 43.2 ± 10.1 | 6.0 |
| Methyl 2 α-deoxy-2β-hydroxyasiatate | 0.1 | 31.2 ± 6.3 | 0.5 |
|  | 1.0 | 66.2 ± 13.6 | 21.8 |
| 2-Tetrahydropyranyl 2-deoxy-3,23-O-diacetyl asiatate | 0.1 | 44.2 ± 11.5 | 6.7 |
|  | 1.0 | 9.5 ± 7.2 | −17.2 |
| Methyl 2-O-methylasiatate | 0.1 | 29.3 ± 5.9 | −3.6 |
|  | 1.0 | 33.9 ± 8.9 | −0.4 |
| Methyl 2-O-ethylasiatate | 0.1 | 37.9 ± 18.2 | 2.3 |
|  | 1.0 | 35.8 ± 13.3 | 0.9 |
| Methyl 2-O-ethyl-11-oxoasiatate | 0.1 | 40.3 ± 14.0 | 3.1 |
|  | 1.0 | 22.3 ± 10.1 | −7.7 |
| 3,23-O-isopropylidene asiatate | 0.1 | 28.4 ± 5.4 | −4.2 |
|  | 1.0 | 22.3 ± 10.1 | −8.4 |
| Octylmethyl 3,23-O-isopropylidene asiatate | 0.1 | 32.3 ± 21.8 | −1.5 |
|  | 1.0 | 21.6 ± 5.0 | −8.9 |
| Ethoxymethyl 3,23-O-isopropylidene asiatate | 0.1 | 46.4 ± 17.8 | 8.2 |
|  | 1.0 | 15.7 ± 9.6 | −12.9 |
| 2α-methyl-2β-hydroxyasiatic acid | 0.1 | 26.8 ± 11.3 | −5.3 |
|  | 1.0 | 60.5 ± 15.7 | 17.9 |
| Octyloxymethyl 3,23-O-benzylidene asiatate | 0.1 | 37.6 ± 7.6 | 2.1 |
|  | 1.0 | 35.8 ± 8.1 | 0.9 |

More excellent anti-dementia effect than Velnacrine (40%) was revealed in the group (75.4%) administered by 2-oxoasiatic acid (1 mg/kg). The group administered by octyloxymethyl 3β,23-dihydroxyurs-12-en-28-oate (1 mg/kg) or methyl 3,23-O-isopropyliden-2-oxoasiatate (0.1 mg/kg) also showed significant anti-dementia effect.

As can be seen from the Experimental Examples described above, the asiatic acid derivatives according to the present invention showed excellent effect on treating dementia and cognitive disorder.

What is claimed is:

1. A method of treating dementia or cognitive disorder comprising administering to a patient in need of such treatment, a therapeutically effective amount of 2-oxoasiatic acid or a pharmaceutically acceptable salt or ester thereof.

* * * * *